United States Patent
Gutekunst et al.

(10) Patent No.: US 6,180,948 B1
(45) Date of Patent: Jan. 30, 2001

(54) IMAGE RECORDING SYSTEM FOR EVALUATING ANALYTICAL TEST ELEMENTS

(75) Inventors: Martin Gutekunst, Eberfing; Hans-Joachim Höltke, Penzberg, both of (DE)

(73) Assignee: Boehringer Mannheim GmbH, Mannheim (DE)

( * ) Notice: Under 35 U.S.C. 154(b), the term of this patent shall be extended for 0 days.

(21) Appl. No.: 09/147,160
(22) PCT Filed: Apr. 23, 1997
(86) PCT No.: PCT/EP97/02065
§ 371 Date: Jan. 25, 1999
§ 102(e) Date: Jan. 25, 1999
(87) PCT Pub. No.: WO97/40368
PCT Pub. Date: Oct. 30, 1997

(30) Foreign Application Priority Data

Apr. 23, 1996 (DE) .............................................. 196 16 151

(51) Int. Cl.[7] ........................... G01N 21/64; G01N 21/76
(52) U.S. Cl. ..................................... 250/458.1; 250/361 C
(58) Field of Search ..................................... 356/317, 318, 356/417; 250/458.1, 459.1, 461.1, 461.2, 361 C (56) References Cited

U.S. PATENT DOCUMENTS 5,672,881 * 9/1997 Striepeke et al. ................. 250/458.1

* cited by examiner

Primary Examiner—F L Evans
(74) Attorney, Agent, or Firm—Arent Fox Kintner Plotkin & Kahn, PLLC (57) ABSTRACT

Image recording system for the evaluation of analytical test elements with a holding unit (8) into which the test elements are placed or onto which they are placed as well as a lens system (5) which records an image of the test elements on a CCD chip (3) and an evaluation unit that evaluates the image on the CCD chip or displays it on a monitor. The image recording system enables numerous test elements of different sizes to be evaluated at different wavelengths without requiring focussing by the user. The lens system used for this is a reducing optical system with an aperture on the side of the image of at least 0.7 and a distance between the CCD chip and the nearest lens of the lens system of less than 15 mm. In addition the distance between the nearest lens of the lens system and the CCD chip is kept constant to at least 10 $\mu$m in order to ensure an adequate sharpness. A compensator is described for keeping this distance constant.

27 Claims, 6 Drawing Sheets

IMAGE RECORDING SYSTEM FOR EVALUATING ANALYTICAL TEST ELEMENTS

The present invention concerns an image recording system for the image recording and evaluation of analytical test elements comprising a holding unit for test elements, a lens system which forms an image of a test element in the holding unit on a CCD chip, a CCD chip, which records an image of the test element and passes it on to an evaluation unit as well as an evaluation unit which converts the signals of the CCD chip into a representation of an image of the test element wherein the focus of the lens system has a fixed setting and the lens system is a reducing optical system with an aperture of at least 0.7 on the image side; the distance between the CCD chip and the nearest lens of the lens system is less than 15 mm and this distance is held constant to at least 10 $\mu$m.

The present invention relates in particular to the field of molecular biology in which biomolecules with a label or dye are detected and their position is determined on a usually flat analytical carrier.

Biomolecules within the sense of the invention are in particular nucleic acids, nucleic acid fragments and proteins.

The labelling and the detection of nucleic acids and proteins is a standard method which is carried out in most biochemical, biological or biomedical laboratories.

Biomolecules can in practice be directly labelled in three different ways:
1. by radioisotopes
2. by fluorescent dyes
3. by colloidal gold.

However, an indirect detection is usually carried out due to the higher sensitivity by labelling the biomolecules with a hapten or biotin and then subsequently detecting by means of antibodies or streptavidin.

The detection proteins (antibody or streptavidin) are then usually coupled to enzymes such as alkaline phosphatase or horseradish peroxidase which catalyse a colour or chemiluminescence reaction via suitable substrates in order to achieve higher detection sensitivities. These reactions are ultimately used for the detection.

Even nowadays radioactive methods are still used considerably more than non-radioactive methods in the field of nucleic acid labelling although they have the disadvantages associated with radioactive isotopes. The major disadvantages are the short half-life of the isotopes as well as the health and environmental hazards of radioactive isotopes. For this reason alternative methods without radioactive isotopes were developed for the labelling of biomolecules. One possibility is to directly couple biomolecules to fluorescent dyes which can then be detected by fluorescence microscopy. However, so-called blotting methods (Southern, Northern and dot blots for nucleic acids and Western blots for proteins) are common in the field of biochemistry. Fluorescent dyes are usually not sufficiently sensitive for these areas of application since problems occur with the signal background and the intrinsic fluorescence of the blotting membranes used. However, a non-radioactive detection is possible on such membranes by direct or indirect binding of the proteins to enzymes such as alkaline phosphatase or peroxidase. Such enzymes catalyse an emission of chemiluminescence light when suitable substrates are added. Similarly nucleic acids can be provided with haptens such as e.g. digoxigenin or biotin and these labels can be detected with specific antibodies which are in turn bound to enzymes.

In methods in which a dye is detected directly, an image of the membrane can be evaluated visually or photographed with standard devices. However, a chemiluminescence reaction is preferably used for the detection processes described above since it is very rapid and very sensitive. It has turned out that a detection by means of a chemiluminescence reaction is at least as sensitive as radioactive detections but can be carried out much more rapidly. At present chemiluminescence signals are recorded by placing an X-ray film on membranes. X-ray films have the advantage that they have a very good resolution and relatively large objects e.g. blots with a size of 40×30 cm can be evaluated. However, a disadvantage of X-ray films is their small dynamic range which is about 2 orders of magnitude and hence is less suitable for distinguishing between strong and weak signals on the same film. For this reason numerous exposures of the same analytical test element are necessary if a quantification of the signals is desired. A further disadvantage of X-ray films is that a special laboratory as well as special chemicals are necessary to develop them and the chemicals have to be disposed of after use.

So-called phosphorus imagers are known in the prior art some of which also record luminescence images. However, the phosphorus imagers are disadvantageous due to their high price as well as the relatively small dynamic range and the low spatial resolution.

Furthermore cooled CCD cameras are on offer in the market for the evaluation of luminescence reactions. However, known instruments have the disadvantage that different optics have to be used for the various sizes of objects that are to be evaluated. In addition it is necessary to focus the optical system in these instruments. Since in biochemical laboratories a large number of analytical test elements such as blots and gels are evaluated, focussing is time-consuming and inconvenient for the operator.

The object of the present invention was to provide a system for evaluating analytical test elements which gives a high sensitivity with an adequate dynamic range and also enables the evaluation of different test elements without requiring a focussing.

The object mentioned above was achieved by an image recording system for the evaluation of analytical test elements. In particular it was found that the object can be achieved when a special lens system is selected which, on the image side, has a high aperture and a small distance from the sensor. However, this is associated on the image side with a very small depth of focus. On the object side a lens system according to the invention has a large depth of focus by which means it is possible to avoid focussing if a holding unit for test elements is present which essentially fixes the distance between the test element and lens system. Due to the large depth of focus on the object side of the lens system used, variations in the distance between the lens system and test element due to variations in the thickness of the test element are insignificant. The problem associated with the lens system according to the invention that the depth of focus is very small on the image side was solved according to the invention by using a compensator which compensates for variations in the distance between the lens system and CCD chip. A further advantage of the system according to the invention is a simplification of the quantitative evaluation by a constant image scale.

The image recording system according to the invention serves to record images of and evaluate analytical test elements. Such test elements are for example membranes on which blotting reactions are carried out or also gels such as those that are for example used for DNA sequencing.

However, those test elements are also suitable according to the invention on which fluorescent or dyed analytes are located. The lens system used in the image recording system is designed so that the advantages are achieved particularly for test elements with a size above ca. 4×4 cm.

The holding unit for flat test elements can for example be a plate on which the test elements are placed. However, the holding unit is preferably in the form of a drawer on the bottom surface of which the test elements are placed and pushed into the image recording system together with the drawer. A holding unit can for example also be composed of guide grooves into which the test element, optionally on a carrier, is inserted. According to the invention the function of the holding unit is to arrange the test elements at an essentially constant distance from the lens system in such a manner that the examination area of the test element is arranged perpendicularly to the optical axis of the lens system and that the test element is positioned laterally such that the area to be evaluated is covered. Due to the special optical system that is used with a large depth of focus on the object side, the distance between the test element and the lens system is, however, less critical so that variations in the range of a few millimetres can be accepted. This is also an important advantage of the image recording system according to the invention since various types of test elements have different thicknesses and also the thickness of test elements of the same type can vary. Therefore according to the invention an adequately focussed image of test elements can be recorded even without having to focus on the special test element present in the system.

It was found that such a system can be realized if a very small distance between the optical system and the CCD chip is selected and the aperture of the lens system on the side facing the CCD chip is enlarged compared to conventional systems. According to the invention the distance between the last lens surface of the lens system and the CCD chip is less than 15 mm, preferably less than 12 mm. The radius of the diaphragm of the lens system on the side facing the CCD chip is larger than 25 mm according to the invention, preferably larger than 30 mm. In order to form a suitable image of test element sizes more than 20×20 cm$^2$ which occur in practice on conventional CCD chips, the lens system is designed as a reducing optical system of 1:n in which n is larger than 10 and preferably larger than 14. Typically the lens system has a focal length of 850 mm and an aperture ratio of 0.95 on the object side. The aperture ratio is given by the quotient of the focal length of the optical system to the diameter of the entrance pupil.

The aperture on the image side of the lens system is at least 0.7 and preferably at least 1.0. The aperture on the image side is understood as the angle of the whole entry pupil in RAD as seen from the image plane.

In order to reduce distortions as much as possible in a lens as described above and in order to achieve a high light intensity, the CCD chip must be brought as close as possible to the lens system. The very small focal length associated with such an arrangement causes the problem that the distance between the CCD chip and the main axis of the lens system must be adjusted extremely accurately and kept constant. With the distance used according to the invention of less than 15 mm or preferably less than 12 mm the distance must be kept constant to at least 10 $\mu$m and preferably to 7 $\mu$m to prevent defocussing. This requirement makes it necessary to have a special construction for the mounting of the image recording system and CCD chip. Methods are described further below for achieving such a constant distance in connection with the compensator.

In order to achieve an adequately high sensitivity and resolution of objects, CCD chips with more than 1000×1000 pixels and pixel sizes of preferably more than 15×15 $\mu$m are preferably used. Suitable CCD chips are commercially available and are therefore not described further.

The images of the test elements recorded by the CCD chip are passed onto an evaluation unit. Such an evaluation unit is usually a microprocessor which is equipped with a unit for signal conversion. Such units are referred to as frame grabbers. When evaluating the images one tries to offer the user a software which is suitable for the respective problem. When evaluating electrophoresis gels the software can for example be used to graphically represent the bands of the analytes that have migrated on the gel and also to quantify them.

As a rule the user of an image recording system according to the invention will be interested in obtaining an image of the test element on which the analytes are visible. For this purpose the evaluation unit produces an image of the test element and for example displays this on a monitor or prints is out on a printer.

As already mentioned the distance between the lens system and CCD chip is unusually small and provisions must be made to keep this distance constant to at least 10 $\mu$m and preferably to 7 $\mu$m. According to the invention this high degree of constancy in the distance can be achieved if the mountings for the CCD chip and lens system as well as the other materials which define the distance between these units are realized by so-called Invar steels which have extremely low thermal coefficients of expansion. However, since these Invar steels are expensive and they are also complicated to machine, other methods are preferred according to the invention to achieve the constancy of distance.

It has turned out to be particularly favourable to use a compensator which compensates thermal changes in the distance between the lens system and CCD chip by an opposing change in length. This can for example be achieved by an arrangement in which the CCD chip rests on the compensator which in turn rests on the holder of the lens system. The arrangement is selected such that when there is a change in temperature the changes in length of the housing and of the compensator are vectorially opposed. In general the compensator is arranged such that a thermal change in distance between the CCD chip and lens system is compensated by a change in length of the compensator. The operating principle of the compensator is elucidated in more detail in FIG. 3 on the basis of an example.

In addition to the already described compensator which does not require measurement of the distance between the lens system and CCD chip, compensators can also be used which make a correction on the basis of a previous measurement of the distance. Such compensators can for example be motor drives, piezo drives or hydraulics. However, according to the invention the lens system is not rotated in order to achieve a focussing as is for example the case in photographic cameras. On the contrary compensators according to the invention directly change the linear distance. Piezo elements are particularly suitable for the necessary changes in length in the micrometer range.

It has turned out to be advantageous to encapsulate the CCD chip in a vacuum. Such an arrangement prevents penetration of dust or humidity. Furthermore it has turned out to be advantageous to place a moisture-absorbing material in the encapsulation such as e.g. silica gel in order to remove residual moisture which could condensate on the lenses or on the sensor. Furthermore it is advantageous to heat the optical window of the encapsulation to prevent condensation of moisture on this window. In addition it is advantageous to also encapsulate the space between the aforementioned window and the lens system (for example $N_2$ atmosphere) in order to prevent heat dissipation and penetration of moisture or dust.

The focal length on the object side is relatively strongly dependent on the light wavelength used in a lens system according to the previous description. It has therefore turned out to be extremely advantageous to select a holding unit which has several holding positions at various distances from the lens system for measurements at various wavelengths. According to the invention it is also possible to use a holding unit which changes the distance between the test element and lens system depending on the wavelength used for the examination. This can for example be achieved by a motor driven table. In the analytical methods for which the image recording system according to the invention is primarily constructed, light of a single wavelength or of a relatively narrow wavelength band is usually evaluated. In luminescence reactions light of only one wavelength normally occurs which is detected. Fluorescence reactions are similar which are irradiated with a first wavelength and the fluorescent light is detected with a second wavelength. A specific evaluation of the luminescent or fluorescent light enables the signal background to be kept low. Hence the image recording system according to the invention is equipped with spectral filters which are transparent for the light to be evaluated but filter out background radiation.

The invention also provides that the system has a light-proof housing which prevents penetration of ambient light. For measurements of fluorescence an illumination unit to excite the fluorescent radiation can be provided within this housing.

The present invention is elucidated in more detail on the basis of the following figures.

FIG. 1 shows a representation of an image recording system according to the invention. The optical unit (1) is located in the upper part of the housing (2). The CCD chip (3) which is cooled by an arrangement of Peltier elements (4) is located within the optical system (1). The heat dissipated by the Peltier elements (4) is removed by a blower. A shutter (6) is located between the lens system (5) and the CCD chip (3) which can prevent light falling on the CCD chip when no measurement is carried out. The power supply (7) and the holding unit (8) for test elements are located in the lower area of the image recording system. The holding unit shown is in the form of a drawer which can be pulled out from the housing. The test elements to be examined are placed on the bottom surface (9) of the drawer and pushed into the housing with the drawer. In addition a glass plate (10) is provided to ensure the test elements lie flat on the bottom surface which lifts up on one side when the drawer is pulled out so that a test element can be inserted under it. When the drawer is pushed in, the glass plate is lowered and presses the test element on the bottom surface (9) of the drawer.

Figure 2:
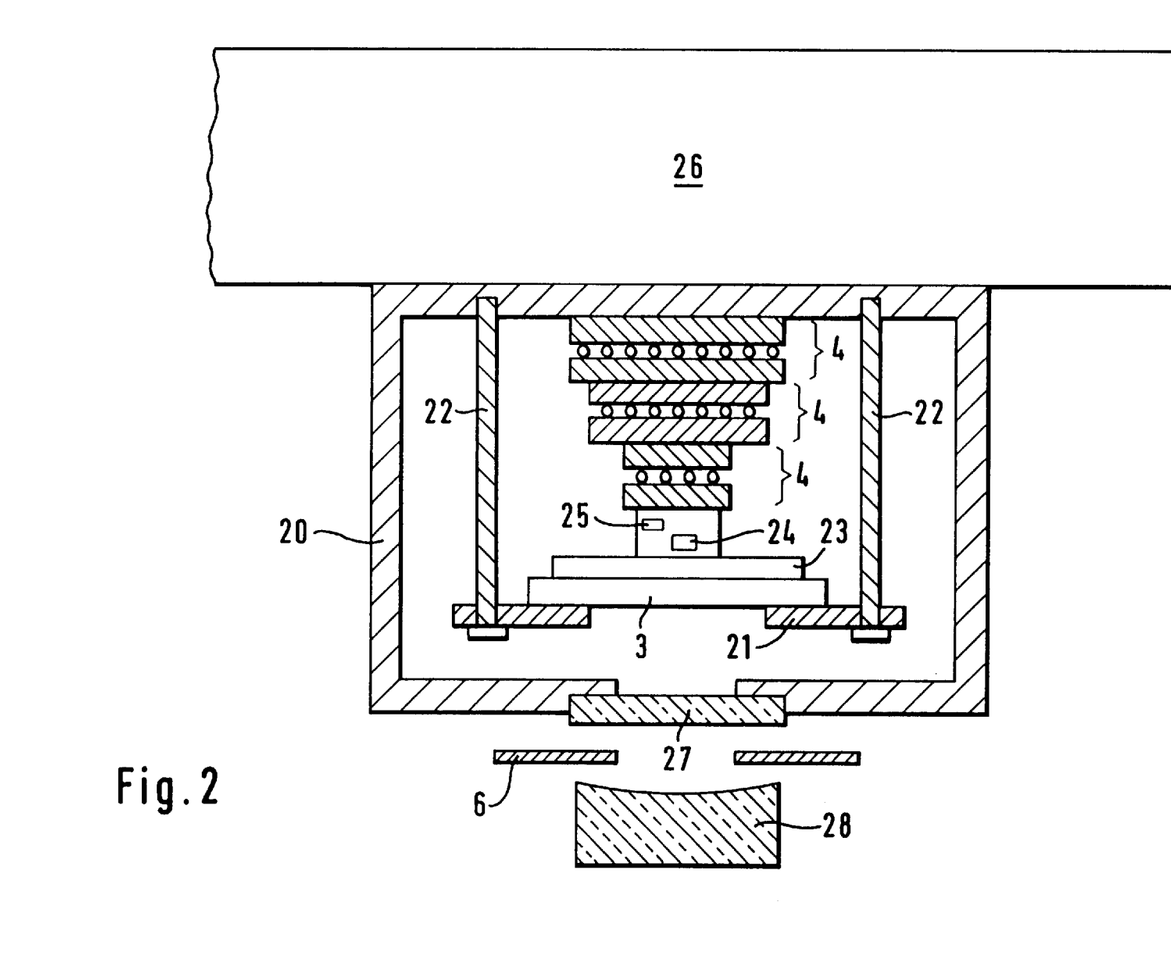
FIG. 2: encapsulated CCD chip

FIG. 2 shows the area of the CCD chip (3) with tempering devices within the encapsulation (20). The CCD chip (3) is located on a holder (21) which in turn is connected to the encapsulation (20) via a spacer (22). The CCD chip (3) is attached to the holder (21) in such a manner that it can be adjusted by rotation around the optical axis and locked in the set position. The CCD chip is fixed onto the cooling block (29) by the spacer (22). An appropriate design of the cooling block ensures a perpendicular position of the chip relative to the optical axis. The cooling block contains the heating resistor (24) and the temperature probe (25). A mounting frame (23) is located above the CCD chip (3) and presses the CCD chip onto the cooling block (29).

A further mounting frame (23) is located above the CCD chip (3) which connects the cooling block (29) to the CCD chip. The unit comprising temperature probe and heating resistor is heat-conductive and is cooled by a cascade of Peltier elements (4). The upper Peltier element transfers the eliminated heat to the encapsulation (20) and the encapsulation in turn transfers it to a cooling plate (26). As already mentioned the cooling plate is preferably cooled by a fan.

An optical window (27) can be seen on the lower side of the encapsulation. The shutter (6) is located between the optical window (27) and the first lens (28) of the lens system (5).

Figure 3:
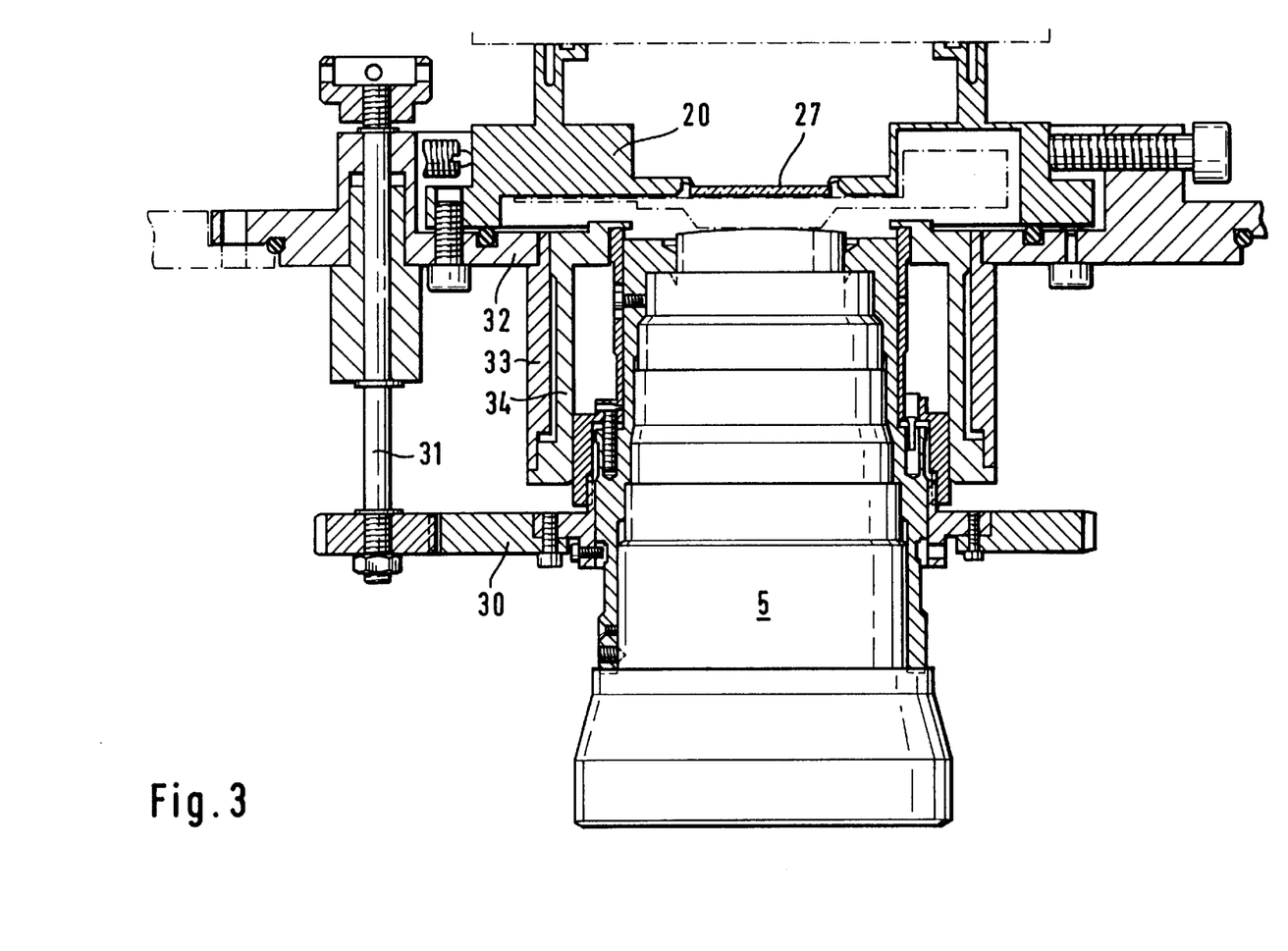
FIG. 3: lens system and CCD chip

FIG. 3 shows the encapsulation (20) with the window (27) and in particular the lens system with holder that adjoins the encapsulation. The lens system is connected to the base plate (32) via a trumpet construction composed of the aluminium cylinder (34) and the steel cylinder (33). The flange plate (32) is flanged onto the encapsulation (20).

The steel cylinder (33) is attached (position 35) to the flange plate (32). The aluminium cylinder (34) is attached to the side of the steel cylinder (position 36) that faces away from the flange and in the plane of the flange only rests on the steel cylinder (position 37). The optical system (5) is attached to the aluminium cylinder in the area near to the flange and is only guided (see guide 39) at the other end of the aluminium cylinder. When heat-dependent changes in the length of the holder arrangement (comprising encapsulation, flange plate, holding pins, holding plate etc.) occur, these are compensated by a change in length of the aluminium cylinder. The principle realized by this arrangement is that a change in length of the holding arrangement is compensated by a change in length of a compensation element (in this case an aluminium cylinder). For this it is necessary that the change in length of the compensation element vectorially opposes the change in length of the remaining holding device. As a rule it would also be necessary that the thermal coefficient of expansion of the compensator is larger than that of the other materials of the holding device. The described embodiment is based on a compensator which compensates on the basis of its thermal change in length. Compensators that either measure the length between the CCD chip and lens system or carry out a temperature measurement and then make the spacing correction are somewhat more complicated but can also be technically accomplished.

The system according to the invention is designed so that the user does not have to focus. However, a focussing is carried out by the manufacturer. This focussing is achieved by means of the adjusting wheel (31) which turns a threaded nut located on the lens system via the gear wheels (30a) and (30). The lens system is preferably itself locked against a rotation. Due to manufacturing tolerances, the lens system can have slight distortions which are not axially symmetrical and thus would also be rotated when the lens system is turned. If in contrast the lens system is secured against twisting then inhomogeneities that may be present can be determined by test samples and optionally compensated by the evaluation unit.

Figure 1:
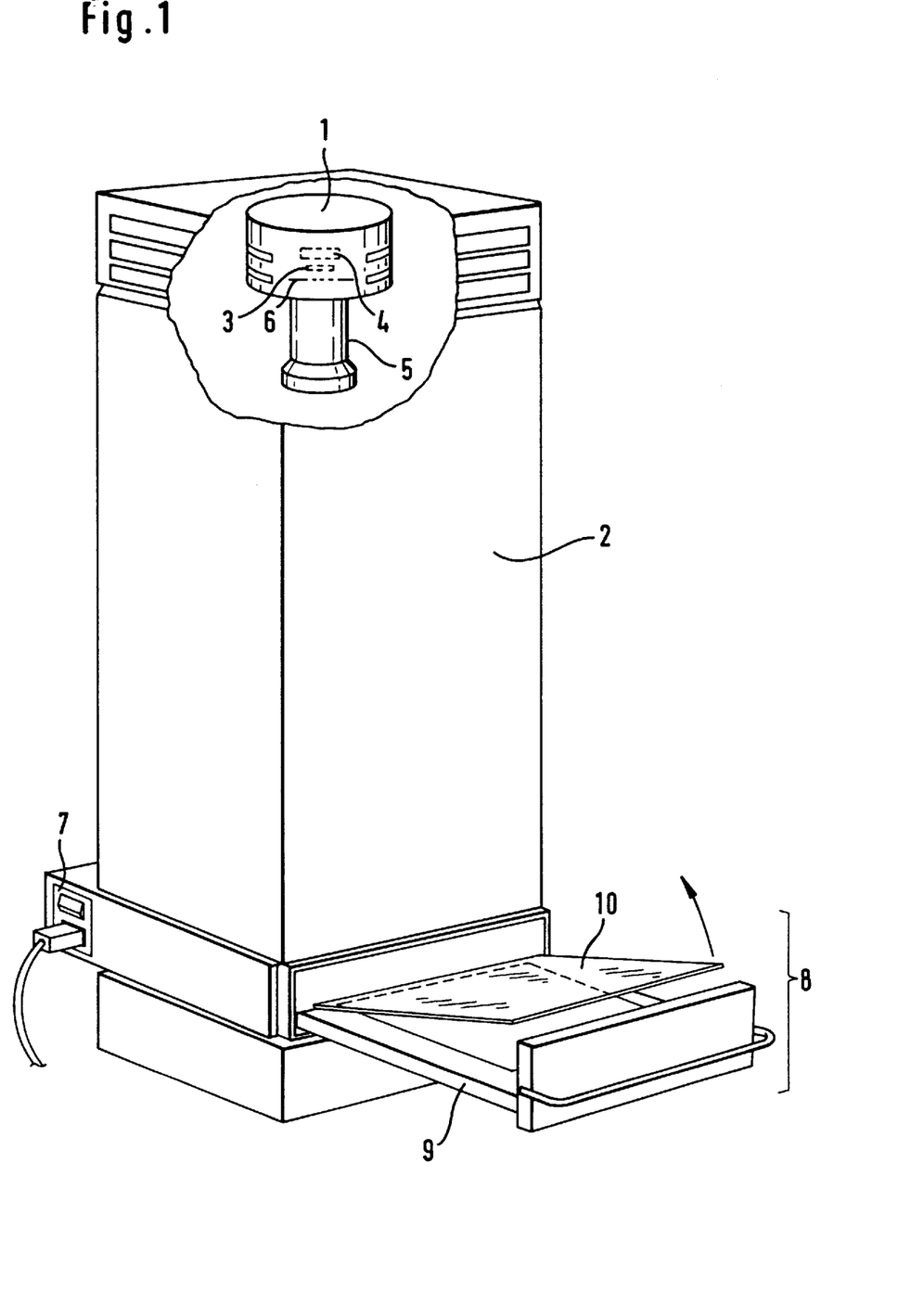
FIG. 1: image recording system
Figure 4:
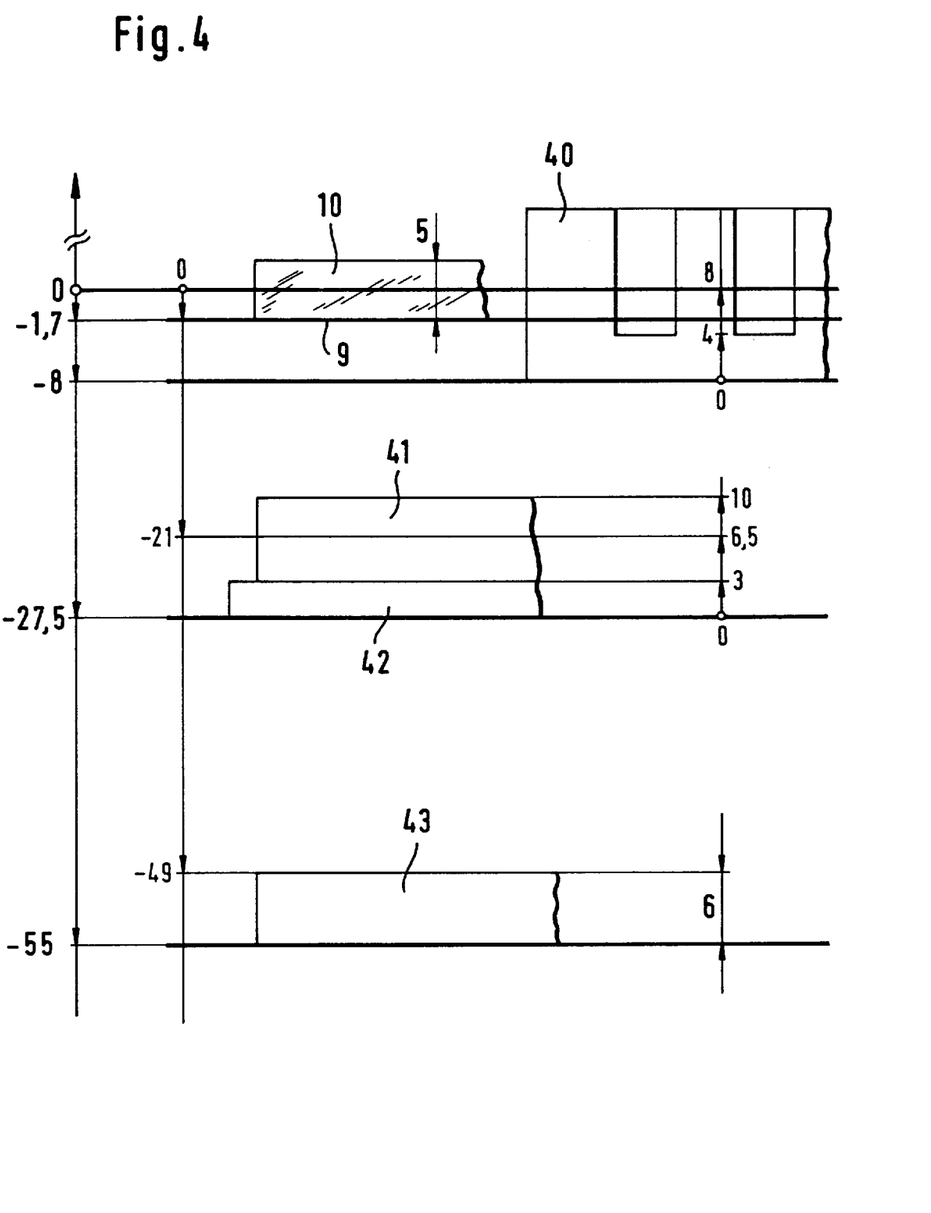
FIG. 4: Schematic representation of a holding unit with several holding positions.

FIG. 4 shows a diagram of various levels that can be achieved in a holding unit. The level labelled "0" on the ordinate is at a distance of 850 mm from the CCD chip. A first plate is located 1.7 mm below this level on which membranes are placed for evaluation by means of a luminescence reaction. This level corresponds to the surface of the base plate (9) of the drawer already shown in FIG. 1. The spacing of this level is selected such that the image recording system yields optimal images for the frequently used luminescence wavelength of 460 nm. However, the system according to the invention cannot only evaluate planar test elements but also for example microtitre plates (40) as shown schematically in FIG. 4. For the evaluation of the microtitre plate (40), a second level can be provided in the holding unit which is at a distance of 8 mm from the zero line. This spacing is selected so that evaluations can be carried out with the liquid levels in the wells of the microtitre plate that occur in practice. A third level is marked at −27.5 mm. This position is particularly suitable for evaluating ethidium bromide gels (41) at 600 nm. Since the ethidium bromide gels are normally evaluated within a trough (42), the height of the trough must be taken into account when selecting the level. A fourth level drawn in FIG. 4 is well-suited for fluorescence measurements at 700 nm. A plate (43) is shown schematically in FIG. 4 which can be electrostatically charged. Membranes can be placed on this plate so that they become attached due to the electrostatic interactions. This type of positioning ensures, similarly to the glass plate (10), that the membranes rest flat on the support and that no errors occur due to rippling.

The distance to the reference level or zero level is shown in FIG. 4 on a first ordinate. The ordinate to the right of this shows the focal levels that are used in each case. When using membranes the focal levels and the support levels essentially coincide. In the example of the ethidium bromide gel (41) the focal level at −21 mm is selected so that it runs through the middle of the gel.

Figure 5:
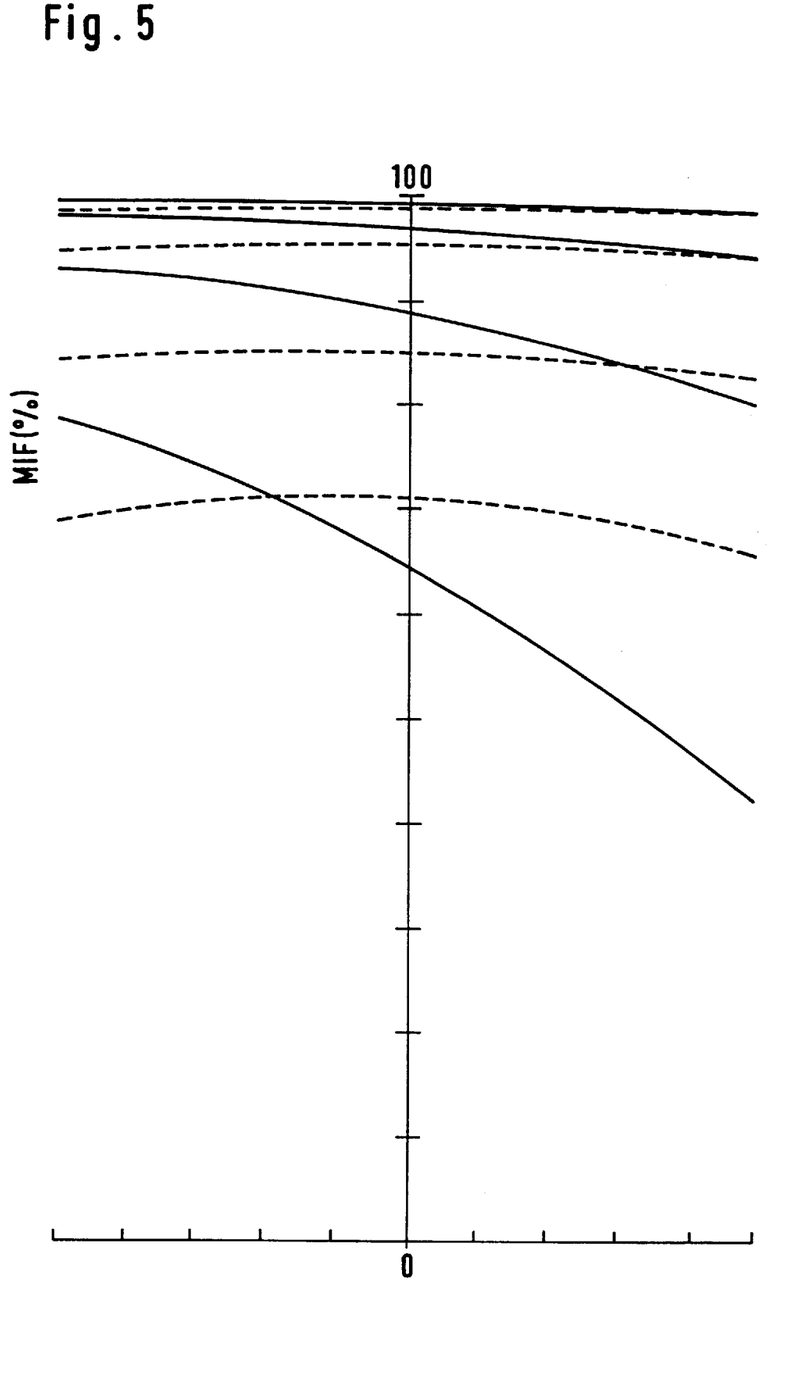
FIG. 5: Defocussing of the optical system for various wavelengths.

FIG. 5 shows a diagram of the defocussing of the image recording system when the distance between the plane of the CCD chip and the lens system is changed. The focussing in the X-direction (continuous lines) and the Y-direction (broken lines) is shown on the ordinate for four different local frequencies. The exact focal plane is shown as zero on the abscissa. Each graduation on the abscissa represents a deviation from the focal plane of 2 µm. Hence FIG. 5 shows how accurately the distance between the CCD chip and lens system must be kept constant for a lens system according to the invention in order to ensure an adequate sharpness.

Figure 6:
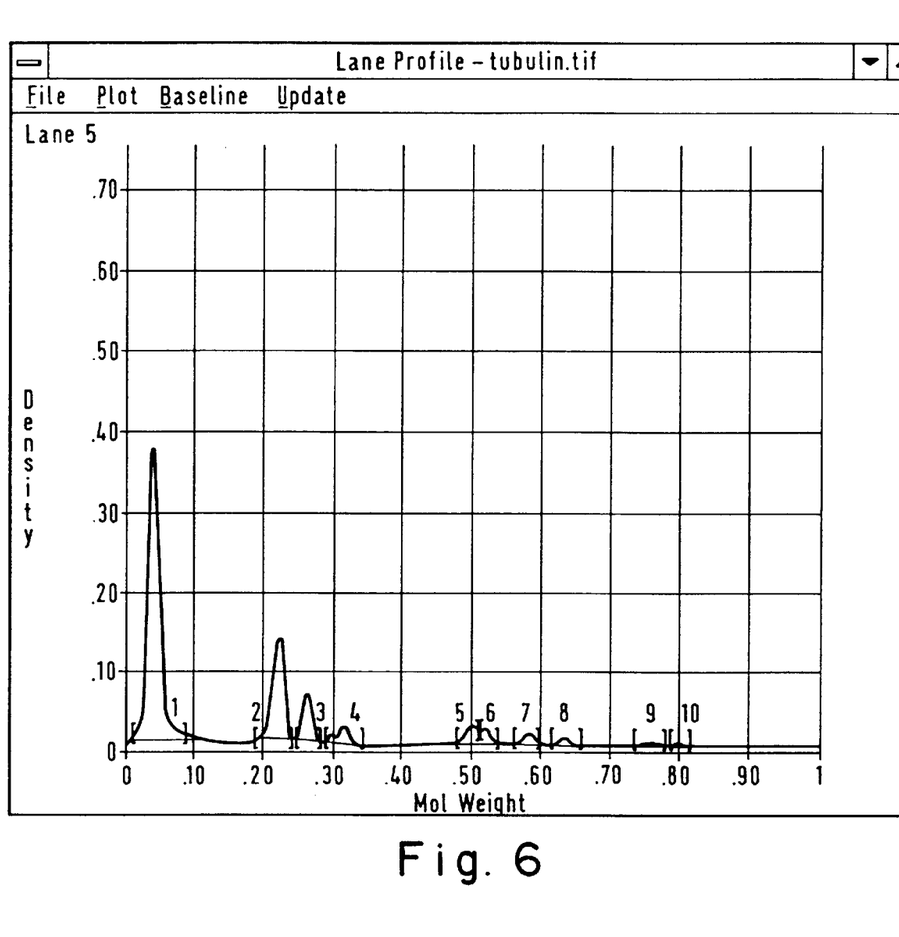
FIG. 6: Photograph of a display of the evaluation of a DNA chemiluminescent blot
Figure 6A:
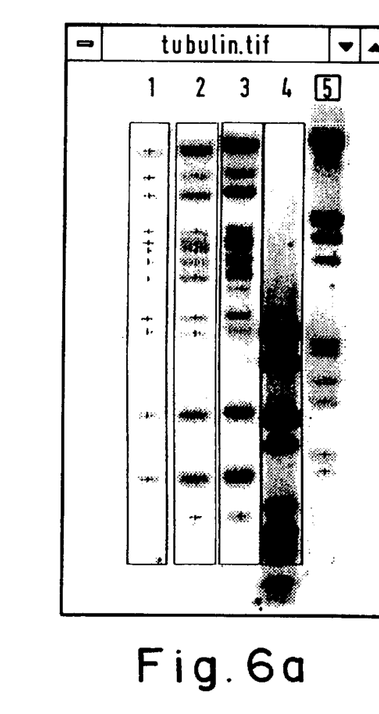

A screen print out of a display of a DNA chemiluminescence blot is shown in FIG. 6. The actual image of the DNA chemiluminescence blot with its bands can be seen in the left half of the picture. The intensities of the bands for the 5th line of the gel is shown to the right of this. The evaluation can be processed with a menu.

List of reference numerals (1) optical system
(2) housing
(3) CCD chip
(4) Peltier elements
(5) lens system
(6) shutter
(7) power supply
(8) holding unit
(9) bottom surface
(10) glass plate
(20) encapsulation
(21) holder for CCD chip
(22) spacer
(23) mounting frame
(24) heating resistor
(25) temperature probe
(26) cooling plate
(27) optical window
(28) first lens
(29) cooling block
(30) gear wheel for focussing
(30a) gear wheel for focussing
(31) adjusting wheel for focussing
(32) flange plate
(33) steel cylinder
(34) aluminium cylinder
(35) site of attachment of the steel cylinder (33)
(36) site at which the aluminium cylinder (34) is attached to the steel cylinder (33)
(37) gliding point of the steel cylinder (33) on the aluminium cylinder (34)
(39) guide
(40) microtitre plate
(51) ethidium bromide gel
(42) trough

What is claimed is:

1. An image recording system for recording images of analytical test elements, said system comprising:
   a holder for holding at least one test element thereupon;
   a lens system including a reducing optical system having an aperture therein, said lens system being configured to provide a focussed image of a test element in the holder;
   a charge coupled device (CCD) disposed a predetermined distance from a nearest lens of said lens system, said charge coupled device being configured to receive and record the focussed image of the test element in the holder as image data;
   an evaluation device connected to said charge coupled device for receiving the image data, and for converting the image data into an image of the test element,
   wherein the lens system provides a permanently set focus, and wherein the aperture on an image side is at least 0.7 RAD, and wherein the predetermined distance between the charge coupled device and the nearest lens is less than 15 mm, and wherein the predetermined distance varies by less than 10 µm.

2. An image recording system as recited in claim 1, wherein the aperture is greater than 1.0 RAD.

3. An image recording system as recited in claim 1, wherein the predetermined distance between the nearest lens of the lens system and the charge coupled device chip is less than 12 mm.

4. An image recording system as recited in claim 1, wherein a radius of the aperture of the lens system is greater than 25 mm.

5. An image recording system as recited in claim 1, wherein a radius of the aperture of the lens system is greater than 30 mm.

6. An image recording system as recited in claim 1, further comprising a compensator disposed between the lens system and the charge coupled device, said compensator configured to compensate for heat-dependent changes in the predetermined distance between the lens system and the charge coupled device.

7. An image recording system as recited in claim 6, wherein the compensator is configured to move one of the lens system and the charge coupled device as a result of thermal expansion and contraction of the compensator, said thermal expansion and contraction being vectorially opposed to a thermal change in length of the distance between the lens system and the charge coupled device.

8. An image recording system as recited in claim 1, wherein the predetermined distance between the charge coupled device and the nearest lens of the lens system is defined by a lens system holder, and wherein a compensator is disposed between the charge coupled device and the lens system holder.

9. An image recording system as recited in claim 5, wherein said compensator is configured to compensate for thermal changes in a length of the lens system holder to maintain the predetermined distance.

10. An image recording system as recited in claim 6, wherein said compensator comprises aluminum.

11. An image recording system as recited in claim 6, wherein said compensator is an active movement device which actively moves to maintain the predetermined distance between the charge coupled device and the nearest lens.

12. An image recording system as recited in claim 11, wherein said compensator comprises a motor drive.

13. An image recording system as recited in claim 11, wherein said compensator comprises a piezo drive.

14. An image recording system as recited in claim 11, wherein said compensator comprises hydraulics.

15. An image recording system as recited in claim 1, further comprising encapsulation adjacent said charge coupled device.

16. An image recording system as recited in claim 15, further comprising moisture-absorbing material disposed within said encapsulation.

17. An image recording system as recited in claim 15, further comprising a heatable window in contact with said encapsulation.

18. An image recording system as recited in claim 1, further comprising an illumination unit for illuminating the test element.

19. An image recording system as recited in claim 1, further comprising a lightproof housing, said lightproof housing containing the test element, the lens system, and the charge coupled device therein.

20. An image recording system as recited in claim 11, wherein said compensator maintains the predetermined distance between the charge coupled device and the nearest lens of the lens system while maintaining a radial position of the lens system.

21. An image recording system as recited in claim 11, wherein said holder comprises at least two holding positions for holding the at least one test element thereupon, said at least two holding positions having different distances to the lens system.

22. An image recording system as recited in claim 1, wherein said holder is configured to hold at least one test element comprising one of gels, membranes, and microtitre plates.

23. An image recording system as recited in claim 1, wherein said evaluation device comprises means for recording and evaluating test elements based upon fluorescence signals.

24. An image recording system as recited in claim 1, wherein said evaluation device comprises means for recording and evaluating test elements based upon chemiluminescence signals.

25. A method of recording images for evaluation of analytical test elements, said method comprising:
provinding an image recording system including a holder for holding at least one test element thereupon, a lens system for providing a focussed image of a test element in the holder, and a charge coupled device adjacent said lens system;
providing a predetermined distance between a nearest lens of the lens system and the charge coupled device;
compensating for thermal changes in the predetermined distance.

26. A method as recited in claim 25, wherein said step of compensating for thermal changes includes providing a compensator between said nearest lens of said lens system and the charge coupled device, said compensator being configured to expand and contract to compensate for the thermal changes in the distance.

27. A method as recited in claim 26, wherein said compensator moves the charge coupled device relative to the nearest lens of the lens system to compensate for the thermal changes in the distance.

* * * * *